US009157857B2

(12) United States Patent
Ono et al.

(10) Patent No.: US 9,157,857 B2
(45) Date of Patent: Oct. 13, 2015

(54) ELECTROMAGNETIC WAVE MEASUREMENT DEVICE, MEASUREMENT METHOD, AND RECORDING MEDIUM

(71) Applicant: ADVANTEST CORPORATION, Tokyo (JP)

(72) Inventors: Shigeru Ono, Miyagi (JP); Kazunori Shiota, Miyagi (JP); Masaichi Hashimoto, Miyagi (JP); Akiyoshi Irisawa, Miyagi (JP)

(73) Assignee: ADVANTEST CORPORATION, Tokyo (JP)

( * ) Notice: Subject to any disclaimer, the term of this patent is extended or adjusted under 35 U.S.C. 154(b) by 0 days.

(21) Appl. No.: 14/108,882

(22) Filed: Dec. 17, 2013

(65) Prior Publication Data

US 2014/0166883 A1   Jun. 19, 2014

(30) Foreign Application Priority Data

Dec. 19, 2012   (JP) ................................ 2012-276428

(51) Int. Cl.
*G01J 5/02* (2006.01)
*G01N 21/59* (2006.01)
*G01B 11/06* (2006.01)

(52) U.S. Cl.
CPC ............ *G01N 21/59* (2013.01); *G01B 11/0633* (2013.01)

(58) Field of Classification Search
CPC .................................................. G01N 21/3586
USPC .................. 250/241.1–341.8, 339.01–339.12
See application file for complete search history.

(56) References Cited

U.S. PATENT DOCUMENTS

2010/0195092 A1* 8/2010 Ohtake ........................... 356/51
2010/0278441 A1* 11/2010 Shashidhar .................. 382/218
2012/0286797 A1  11/2012 Kato et al.

FOREIGN PATENT DOCUMENTS

JP       2012-237657     12/2012

OTHER PUBLICATIONS

Hasegawa et al., "Thickness measurement of iron-oxide layers on steel plates using terahertz reflectometry,", 2011, 36th International Conference on Infrared, Millimeter and Terahertz Waves, IEEE, pp. 1-2.*
Feige et al., "Non-Contact Multilayer Thickness Measurements with Reflection-Mode Terahertz Time-Domain Spectroscopy," 2011, Lasers and Electro-Optics Europe (CLEO EUROPE/EQEC), 2011 Conference on and 12th Eupopean Quantum Electronics Conference, p. 1.*

* cited by examiner

*Primary Examiner* — Kiho Kim
(74) *Attorney, Agent, or Firm* — Greenblum & Bernstein P.L.C.

(57) ABSTRACT

According to the present invention, an electromagnetic wave measurement device includes: an electromagnetic wave detector, a frequency component acquisition unit, and a thickness indication quantity deriving unit. An object to be measured is disposed on a substrate and includes at least two layers, and the electromagnetic wave detector detects a substrate-surface-reflected electromagnetic wave which has been made incident to the object, has been reflected by the substrate, and has passed through the object. The frequency component acquisition unit acquires an amplitude of a frequency component of the substrate-surface-reflected electromagnetic wave. The thickness indication quantity deriving unit derives a thickness indication quantity based on the amplitude of the frequency component of the substrate-surface-reflected electromagnetic wave and a relationship between the thickness indication quantity and the amplitude of the frequency component of the substrate-surface-reflected electromagnetic wave.

9 Claims, 12 Drawing Sheets (a)

(b)

(a)

(b)

(a)

(b)

(a)

(b)

ELECTROMAGNETIC WAVE MEASUREMENT DEVICE, MEASUREMENT METHOD, AND RECORDING MEDIUM

BACKGROUND OF THE INVENTION

1. Field of the Invention

The present invention relates to a measurement of a specimen having a layered structure without destroying the layers using an electromagnetic wave (the frequency of which is between 0.01 [THz] and 100 [THz]) (such as a terahertz wave (the frequency of which is between 0.03 [THz] and 10 [THz]), for example).

2. Related Art

There is a known technique of irradiating a specimen having a layered structure with a terahertz wave and detecting reflected terahertz waves reflected by respective layers in order to test the specimen by means of non-destructive test (refer to Abstract of JP 2012-237657 A, for example).

SUMMARY OF THE INVENTION

However, a wave reflected by an interface between layers may not be measured. For example, if refractive indices of the respective neighboring layers are almost equal to each other, the reflected wave by the boundary surface between the layers may not be measured. Moreover, if the lowest layer of the specimen is placed on a metal surface, a reflected wave by the metal surface becomes strong. Therefore, a reflected wave by a boundary surface between layers close to the lowest layer of the specimen may not be distinguished from the reflected wave by the metal surface. Thus, the reflected wave by the boundary surface may not be measured. In this case, the conventional technique cannot test a specimen.

It is therefore an object of the present invention to measure an object to be measured having a layered structure by irradiating an electromagnetic wave on the object to be measured without measuring the reflected wave by a boundary surface between layers.

According to the present invention, an electromagnetic wave measurement device includes: an electromagnetic wave output device that outputs an electromagnetic wave having a frequency between 0.01 [THz] and 100 [THz] toward an object to be measured disposed on a substrate and including at least two layers; an electromagnetic wave detector that detects a substrate-surface-reflected electromagnetic wave which has been made incident to the object to be measured, has been reflected by the substrate, and has passed through the object to be measured; a frequency component acquisition unit that acquires an amplitude of a frequency component of the substrate-surface-reflected electromagnetic wave detected by the electromagnetic wave detector; a thickness/amplitude characteristic recording unit that records a relationship between a thickness indication quantity representing a thickness of at least any one of the layers of the object to be measured, and the amplitude of the frequency component of the substrate-surface-reflected electromagnetic wave; and a thickness indication quantity deriving unit that derives a thickness indication quantity based on the amplitude of the frequency component of the substrate-surface-reflected electromagnetic wave acquired by the frequency component acquisition unit and the recorded content of the thickness/amplitude characteristic recording unit.

According to the thus constructed electromagnetic wave measurement device, an electromagnetic wave output device outputs an electromagnetic wave having a frequency between 0.01 [THz] and 100 [THz] toward an object to be measured disposed on a substrate and including at least two layers. An electromagnetic wave detector detects a substrate-surface-reflected electromagnetic wave which has been made incident to the object to be measured, has been reflected by the substrate, and has passed through the object to be measured. A frequency component acquisition unit acquires an amplitude of a frequency component of the substrate-surface-reflected electromagnetic wave detected by the electromagnetic wave detector. A thickness/amplitude characteristic recording unit records a relationship between a thickness indication quantity representing a thickness of at least any one of the layers of the object to be measured, and the amplitude of the frequency component of the substrate-surface-reflected electromagnetic wave. A thickness indication quantity deriving unit derives a thickness indication quantity based on the amplitude of the frequency component of the substrate-surface-reflected electromagnetic wave acquired by the frequency component acquisition unit and the recorded content of the thickness/amplitude characteristic recording unit.

According to the electromagnetic wave measurement device of the present invention, the recorded content of the thickness/amplitude characteristic recording unit may be derived based on reflection and absorption of the electromagnetic wave in each of the layers.

According to the electromagnetic wave measurement device of the present invention, the recorded content of the thickness/amplitude characteristic recording unit may be estimated from a measured value of the amplitude of the frequency component of the substrate-surface-reflected electromagnetic wave associated with the known thickness indication quantity.

According to the electromagnetic wave measurement device of the present invention, the thickness indication quantity may be a value acquired by dividing the thickness of any one of the layers by a thickness of the object to be measured.

According to the electromagnetic wave measurement device of the present invention, the thickness indication quantity may be a value acquired by dividing the thickness of any one of the layers by the thickness of another layer.

According to the electromagnetic wave measurement device of the present invention, the substrate may be a metal plate.

According to the present invention, the electromagnetic wave measurement device may include: an error variation deriving unit that derives, from a measured value of the amplitude of the frequency component of the substrate-surface-reflected electromagnetic wave associated with the known thickness indication quantity, a variation of an error between a thickness indication quantity acquired based on the recorded content of the thickness/amplitude characteristic recording unit and the known thickness indication quantity for each of frequency components; and a frequency range determination unit that determines a range of the frequency of the amplitude of the frequency component acquired by the frequency component acquisition unit based on the derived result by the error variation deriving unit.

According to the electromagnetic wave measurement device of the present invention, the electromagnetic wave detector may further detect a surface-reflected electromagnetic wave which is an electromagnetic wave that has been made incident to the object to be measured and has been reflected by a surface of the object to be measured, the electromagnetic wave measurement device including: an extreme value timing acquisition unit that acquires timings when electric fields of the substrate-surface-reflected electromagnetic wave and the surface-reflected electromagnetic wave that have been detected by the electromagnetic wave detector take extreme values; a total thickness deriving unit that derives a thickness of the object to be measured from a time difference between the timings acquired by the extreme value timing acquisition unit; and a layer thickness deriving unit that derives a thickness of at least any one of the layers of the object to be measured based on the thickness indication quantity derived by the thickness indication quantity deriving unit and the thickness of the object to be measured derived by the total thickness deriving unit.

According to the present invention, an electromagnetic wave measurement method includes: an electromagnetic wave output step that outputs an electromagnetic wave having a frequency between 0.01 [THz] and 100 [THz] toward an object to be measured disposed on a substrate and including at least two layers; an electromagnetic wave detection step that detects a substrate-surface-reflected electromagnetic wave which has been made incident to the object to be measured, has been reflected by the substrate, and has passed through the object to be measured; a frequency component acquisition step that acquires an amplitude of a frequency component of the substrate-surface-reflected electromagnetic wave detected by the electromagnetic wave detection step; a thickness/amplitude characteristic recording step that records a relationship between a thickness indication quantity representing a thickness of at least any one of the layers of the object to be measured, and the amplitude of the frequency component of the substrate-surface-reflected electromagnetic wave; and a thickness indication quantity deriving step that derives a thickness indication quantity based on the amplitude of the frequency component of the substrate-surface-reflected electromagnetic wave acquired by the frequency component acquisition step and the recorded content of the thickness/amplitude characteristic recording step.

The present invention is a program of instructions for execution by a computer to perform a electromagnetic wave measurement process with using an electromagnetic wave measurement device including an electromagnetic wave output device that outputs an electromagnetic wave having a frequency between 0.01 [THz] and 100 [THz] toward an object to be measured disposed on a substrate and including at least two layers, and an electromagnetic wave detector that detects a substrate-surface-reflected electromagnetic wave which has been made incident to the object to be measured, has been reflected by the substrate, and has passed through the object to be measured, the electromagnetic wave measurement process including: a frequency component acquisition step that acquires an amplitude of a frequency component of the substrate-surface-reflected electromagnetic wave detected by the electromagnetic wave detector; a thickness/amplitude characteristic recording step that records a relationship between a thickness indication quantity representing a thickness of at least any one of the layers of the object to be measured, and the amplitude of the frequency component of the substrate-surface-reflected electromagnetic wave; and a thickness indication quantity deriving step that derives a thickness indication quantity based on the amplitude of the frequency component of the substrate-surface-reflected electromagnetic wave acquired by the frequency component acquisition step and the recorded content of the thickness/amplitude characteristic recording step.

The present invention is a computer-readable medium having a program of instructions for execution by a computer to perform a electromagnetic wave measurement process with using an electromagnetic wave measurement device including an electromagnetic wave output device that outputs an electromagnetic wave having a frequency between 0.01 [THz] and 100 [THz] toward an object to be measured disposed on a substrate and including at least two layers, and an electromagnetic wave detector that detects a substrate-surface-reflected electromagnetic wave which has been made incident to the object to be measured, has been reflected by the substrate, and has passed through the object to be measured, the electromagnetic wave measurement process including: a frequency component acquisition step that acquires an amplitude of a frequency component of the substrate-surface-reflected electromagnetic wave detected by the electromagnetic wave detector; a thickness/amplitude characteristic recording step that records a relationship between a thickness indication quantity representing a thickness of at least any one of the layers of the object to be measured, and the amplitude of the frequency component of the substrate-surface-reflected electromagnetic wave; and a thickness indication quantity deriving step that derives a thickness indication quantity based on the amplitude of the frequency component of the substrate-surface-reflected electromagnetic wave acquired by the frequency component acquisition step and the recorded content of the thickness/amplitude characteristic recording step.

BRIEF DESCRIPTION OF DRAWINGS

11(*b*)) showing timings when temporal waveforms of the reflected electromagnetic waves take extreme values.

DETAILED DESCRIPTION OF THE INVENTION

Figure 1:
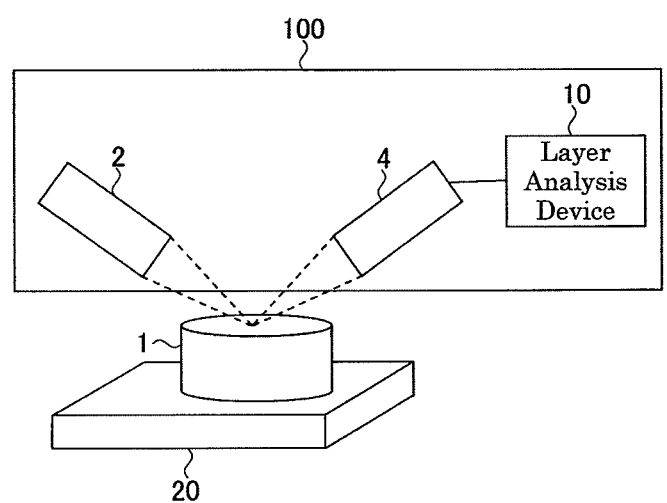
FIG. 1 is a diagram showing a configuration of an electromagnetic wave measurement device 100 according to an embodiment of the present invention.

A description will now be given of embodiments of the present invention referring to the drawings.

First Embodiment

Figure 2:
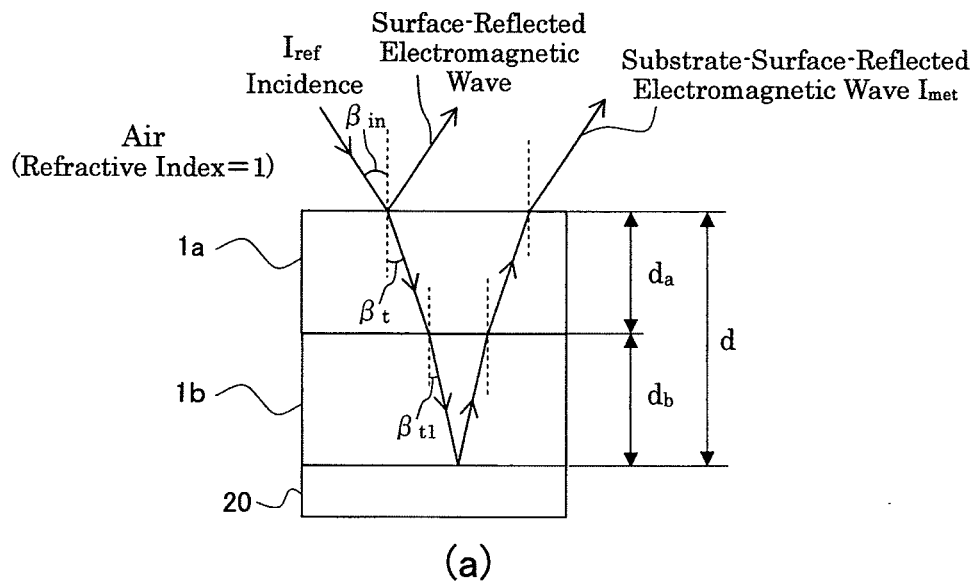
FIG. 2 includes a diagram (refer to FIG. 2(a)) showing an electromagnetic wave reflected by an object to be measured 1 having a two-layer structure and a substrate 20, and a diagram (refer to FIG. 2(b)) showing a temporal waveform of the reflected electromagnetic waves.
Figure 2:
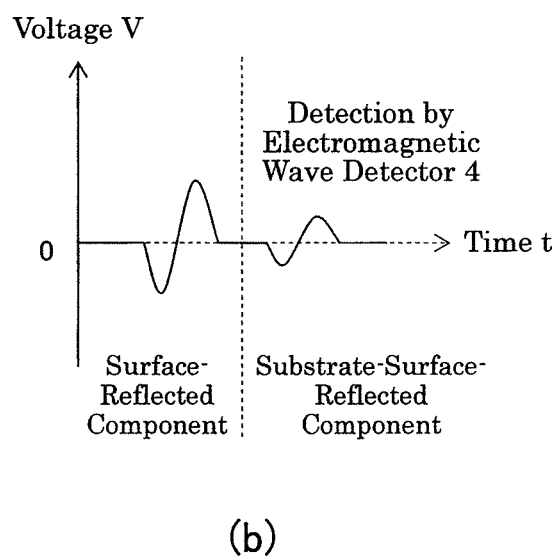

FIG. 1 is a diagram showing a configuration of an electromagnetic wave measurement device 100 according to an embodiment of the present invention. FIG. 2 includes a diagram (refer to FIG. 2(*a*)) showing an electromagnetic wave reflected by an object to be measured 1 having a two-layer structure and a substrate 20, and a diagram (refer to FIG. 2(*b*)) showing a temporal waveform of the reflected electromagnetic waves.

The electromagnetic measurement device 100 according to the embodiment of the present invention includes an electromagnetic wave output device 2, an electromagnetic wave detector 4, and a layer analysis device 10. The electromagnetic wave measurement device 100 is used for measuring the object to be measured 1.

The object to be measured 1 includes a layer 1*a* and a layer 1*b* referring to FIG. 2(*a*). The layer 1*a* is above the layer 1*b*. It should be noted that the object to be measured 1 is placed on the substrate 20, and the layer 1*b* is in contact with the substrate 20. For example, the substrate 20 is a metal plate (the material is aluminum, for example), and a flat surface of the metal plate is in contact with the layer 1*b*. The flat surface of the metal plate serves as a flat surface mirror. The substrate 20 only needs to be a substrate having a known complex refractive index, and is preferably high in reflectance of an interface between the substrate 20 and the layer 1*b*.

Although the object to be measured 1 has two layers according to the embodiment of the present invention, the object to be measured 1 may have three or more layers.

The electromagnetic wave output device 2 outputs an electromagnetic wave having a frequency between 0.01 [THz] and 100 [THz] toward the object to be measured 1. The frequency of the electromagnetic wave output toward the object to be measured 1 includes a terahertz wave band (such as between 0.03 [THz] and 10 [THz]). According to all embodiments of the present invention, it is assumed that a terahertz wave is employed as an example of the electromagnetic wave.

Referring to FIG. 2(*a*), the terahertz wave output toward the object to be measured 1, travels in the air (refractive index=1), and is made incident to the object to be measured 1. A part of the terahertz wave passes through the layer 1*a*, enters the layer 1*b*, is reflected by the substrate 20, passes through the layer 1*b*, further passes through the layer 1*a* (passes through the object to be measured 1), and is emitted from the object to be measured 1 toward the outside. In other words, the terahertz wave is made incident to the object to be measured 1, is reflected by the substrate 20, and passes through the object to be measured 1. The electromagnetic wave (such as a terahertz wave) which has passed through the object to be measured 1 in this way is referred to as substrate-surface-reflected electromagnetic wave.

The electromagnetic wave detector 4 detects the substrate-surface-reflected electromagnetic wave. It should be noted that electromagnetic waves reflected by surfaces other than the substrate 20 (such as a terahertz wave reflected by a surface of the layer 1*a* (referred to as surface-reflected electromagnetic wave)) in addition to the substrate-surface-reflected electromagnetic wave enter the electromagnetic wave detector 4.

However, referring to FIG. 2(*b*), the surface-reflected electromagnetic wave reaches the electromagnetic wave detector 4 earlier than the substrate-surface-reflected electromagnetic wave. As a result, the surface-reflected electromagnetic wave and the substrate-surface-reflected electromagnetic wave can be distinguished from each other. In other words, the electromagnetic wave which has reached later out of the reflected electromagnetic waves is the substrate-surface-reflected electromagnetic wave.

An electromagnetic wave reflected by a boundary surface between the layers 1*a* and 1*b* does not need to be measured, and is not specifically considered to be as a subject to detection (may basically be undetectable).

The electromagnetic wave detector 4 outputs a correspondence between the substrate-surface-reflected electromagnetic wave and the time (namely temporal waveform). The electromagnetic wave detector 4 detects the substrate-surface-reflected electromagnetic wave as a voltage (or power), for example. A description will be given while it is assumed that the electromagnetic wave detector 4 detects the substrate-surface-reflected electromagnetic wave as a voltage according to the embodiment of the present invention.

Figure 3:
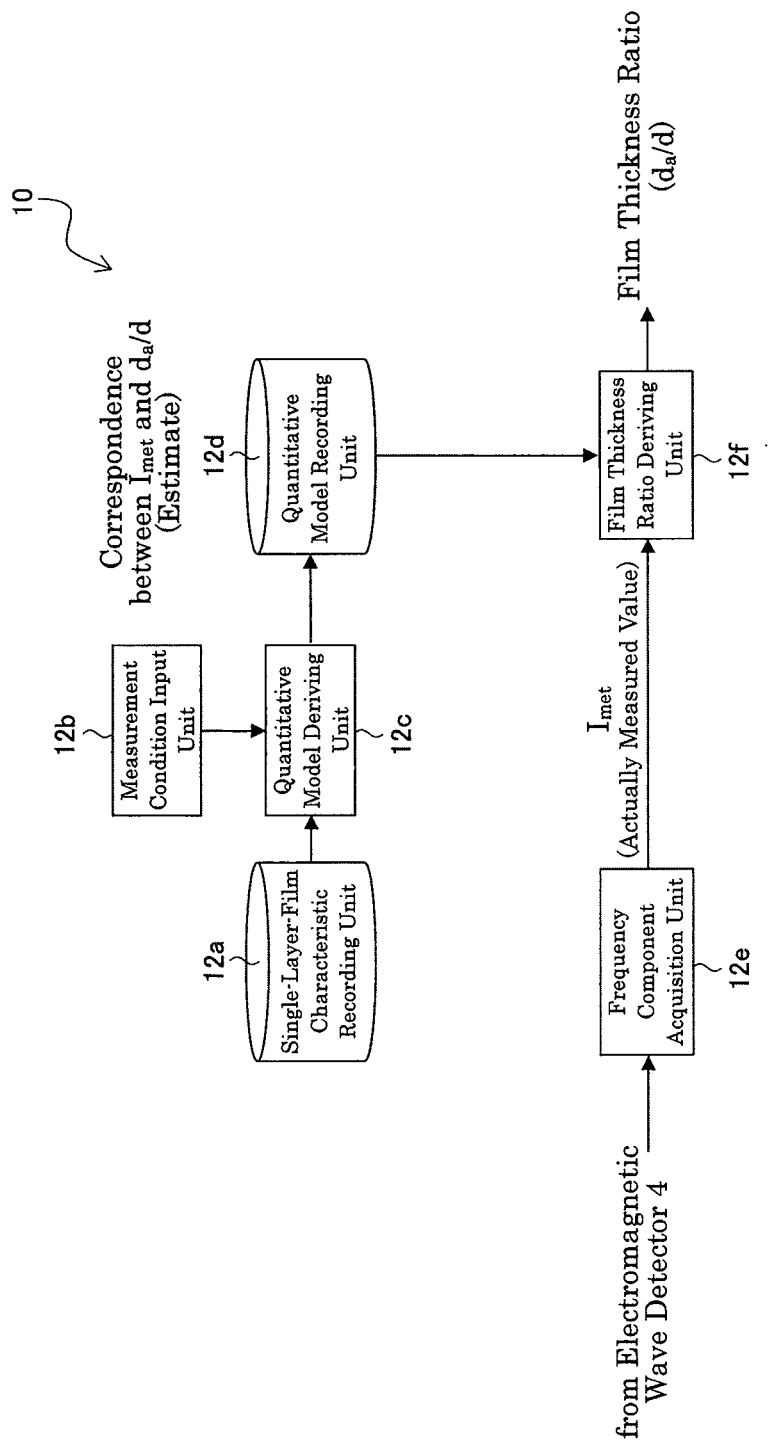
FIG. 3 is a functional block diagram showing a configuration of the layer analysis device 10 according the first embodiment.

FIG. 3 is a functional block diagram showing a configuration of the layer analysis device 10 according the first embodiment. The layer analysis device 10 includes a single-layer-film characteristic recording unit 12*a*, a measurement condition input unit 12*b*, a quantitative model deriving unit 12*c*, a quantitative model recording unit (thickness/amplitude characteristic recording unit) 12*d*, a frequency component acquisition unit 12*e*, and a film thickness ratio deriving unit (thickness indication quantity deriving unit) 12*f*.

The single-layer-film characteristic recording unit 12*a* records characteristics relating to the reflection and absorption of the terahertz wave of the layers 1*a* and 1*b*. For example, the single-layer-film characteristic recording unit 12*a* records an absorption coefficient, a surface reflectance, and an interface reflectance of the terahertz wave on the layers 1*a* and 1*b*.

The recorded content of the single-layer-film characteristic recording unit 12*a* can be generated by an arbitrary measurement device carrying out the following measurement.

First, the electromagnetic wave output device 2 acquires an amplitude of a frequency component of a terahertz wave to be made incident to the object to be measured 1.

Figure 4:
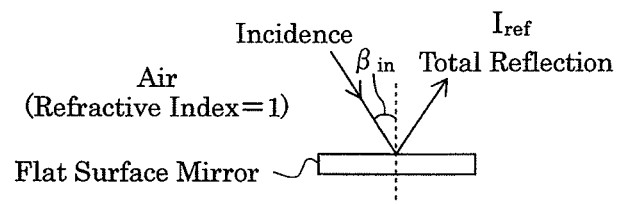
FIG. 4 includes diagrams describing the acquisition of the amplitudes of the frequency components of the terahertz wave to be made incident to the object to be measured 1 by the electromagnetic wave output device 2, and shows an optical path of a totally reflected terahertz wave (refer to FIG. 4(a)), and a temporal waveform of the totally reflected terahertz wave (refer to FIG. 4(b))
Figure 4:
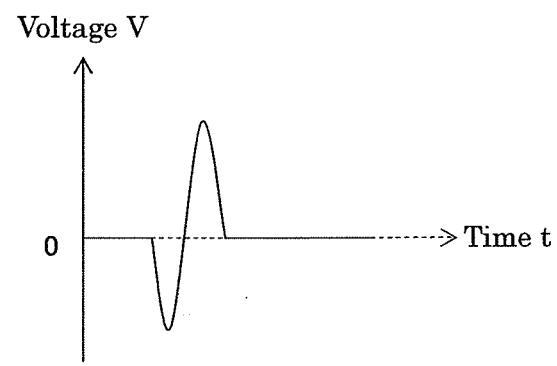

FIG. 4 includes diagrams describing the acquisition of the amplitudes of the frequency components of the terahertz wave to be made incident to the object to be measured 1 by the electromagnetic wave output device 2, and shows an optical path of a totally reflected terahertz wave (refer to FIG. 4(*a*)), and a temporal waveform of the totally reflected terahertz wave (refer to FIG. 4(*b*)).

First, if the terahertz wave traveling in the air (refractive index=1) is made incident to a flat surface mirror at an arbitrary incident angle of θin as shown in FIG. 4(*a*), the terahertz wave is totally reflected. The totally reflected terahertz wave is detected as a voltage, for example, resulting in acquisition of a temporal waveform of the terahertz wave. Then, the temporal waveform of the totally reflected terahertz wave is acquired as shown in FIG. 4(*b*). Amplitudes of frequency components are acquired by applying the FFT (fast Fourier transform) to the terahertz wave represented by the temporal waveform. In other words, the totally reflected terahertz wave is expressed as a sum of frequency components $A_n$ sin ($2\pi f \cdot nt + \theta_n$) by means of the FFT, and the amplitude $A_n$ is acquired for each frequency f·n. It should be noted that n is an integer taking all values between 0 and N, N is a positive integer, f is a predetermined frequency [Hz], and $\theta_n$ is a phase of the frequency component. The amplitude of the frequency component of the totally reflected terahertz wave is represented as $I_{ref}$.

For example, if f is 0.1 [THz] and N is 30, the totally reflected terahertz wave is represented as a sum of a component of a frequency 0 THz, a component of a frequency 0.1 THz, a component of a frequency 0.2 THz, ..., a component of a frequency 2.9 THz, and a component of a frequency 3.0 THz, and amplitudes $I_{ref}$ (0 THz), $I_{ref}$ (0.1 THz), $I_{ref}$ (0.2 THz), ..., $I_{ref}$ (2.9 THz), and $I_{ref}$ (3.0 THz) for the respective frequency components.

The amplitude $I_{ref}$ is acquired for the each frequency component, and is thus a function of the frequency. The frequency is described as an argument of the amplitude $I_{ref}$ in the above-mentioned example. However, the frequency is omitted as the argument of the amplitude $I_{ref}$ hereinafter.

Figure 5:
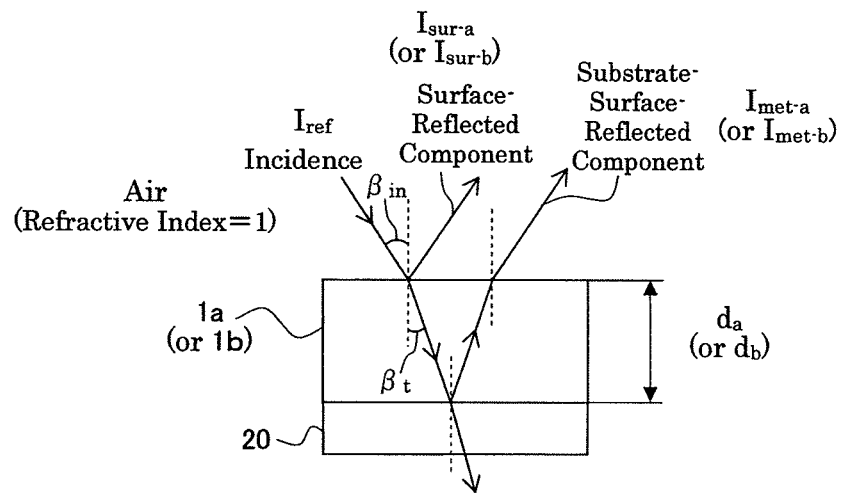
FIG. 5 includes a diagram showing an optical paths when a terahertz wave to be made incident to the object to be measured 1 by the electromagnetic wave output device 2 is made incident to the layer 1a or the layer 1b (refer to FIG. 5(a)), and a diagram of a temporal waveform of reflected terahertz waves (refer to FIG. 5(b))
Figure 5:
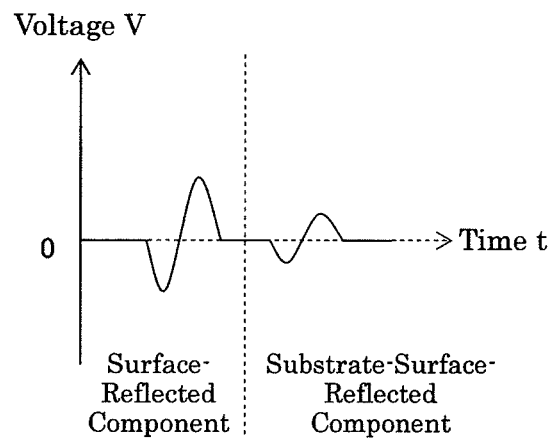

FIG. 5 includes a diagram showing an optical paths when a terahertz wave to be made incident to the object to be measured 1 by the electromagnetic wave output device 2 is made incident to the layer 1a or the layer 1b (refer to FIG. 5(a)), and a diagram of a temporal waveform of reflected terahertz waves (refer to FIG. 5(b)).

On this occasion, the terahertz wave to be made incident to the object to be measured 1 by the electromagnetic wave output device 2 is caused to travel in the air (refractive index=1), and to actually be made incident to the layer 1a. It should be noted that the layer 1a is placed on the substrate 20. On this occasion, an amplitude $I_{sur-a}$ of a frequency component of the terahertz wave reflected by a surface of the layer 1a (surface-reflected component), and an amplitude $I_{met-a}$ of the frequency component of the terahertz wave reflected by an interface between the layer 1a and the substrate 20 (substrate-surface-reflected component) are measured.

Further, the terahertz wave to be made incident to the object to be measured 1 by the electromagnetic wave output device 2 is caused to travel in the air (refractive index=1), and to actually be made incident to the layer 1b. It should be noted that the layer 1b is placed on the substrate 20. On this occasion, an amplitude $I_{sur-b}$ of the frequency component of the terahertz wave (surface-reflected component) reflected by a surface of the layer 1b, and an amplitude $I_{met-b}$ of the frequency component of the terahertz wave (substrate-surface-reflected component) reflected by an interface between the layer 1b and the substrate 20 are measured.

It should be noted that the same terahertz wave as the terahertz wave totally reflected in FIG. 4 is made incident to the layer 1a or the layer 1b in FIG. 5.

Referring to FIG. 5(a), if the terahertz wave is made incident to the layer 1a (or layer 1b), the component reflected by the surface of the layer 1a (surface-reflected component), and the component reflected by the interface between the layer 1a and the substrate 20 (substrate-surface-reflected component) are acquired. The surface-reflected component and the substrate-surface-reflected component are acquired as voltages, thereby acquiring temporal waveform thereof. Then, the temporal waveform of the surface-reflected component and the substrate-surface-reflected component are acquired as shown in FIG. 5(b).

Referring to FIG. 5(b), the surface-reflected component is detected earlier than the substrate-surface-reflected component. As a result, the surface-reflected component and the substrate-surface-reflected component can be distinguished from each other. In other words, out of the reflected components, the component arriving earlier is the surface-reflected component, and the component arriving later is the substrate-surface-reflected component.

The FFT (fast Fourier transform) is applied to the terahertz wave represented as the temporal wave of the surface-reflected component by the layer 1a (layer 1b), thereby acquiring amplitudes $I_{sur-a}$ ($I_{sur-b}$) of frequency components of the surface-reflected component by the layer 1a (layer 1b). The amplitude of the frequency component is described as the description given of the $I_{ref}$. The description of frequency is omitted for the argument of the amplitude $I_{sur-a}$ ($I_{sur-b}$) of the frequency component of the surface-reflected component as for the description for the $I_{ref}$.

The FFT (fast Fourier transform) is applied to the terahertz wave represented as the temporal wave of the substrate-surface-reflected component by the layer 1a (layer 1b), thereby acquiring amplitudes $I_{met-a}$ ($I_{met-b}$) of frequency components of the substrate-surface-reflected component by the layer 1a (layer 1b). The amplitude of the frequency component is the same as described for the $I_{ref}$. The frequency is omitted for the argument of the amplitude $I_{met-a}$ ($I_{met-b}$) of the frequency component of the surface-reflected component as the notation for the $I_{ref}$.

An absorption coefficient $\alpha_a$ of the terahertz wave and a surface reflectance $R_{sur-a}$ of the terahertz wave in the layer 1a recorded by the single-layer-film characteristic recording unit 12a are as follows. It should be noted that, referring to FIG. 5(a), a refraction angle $\beta_t$ can be derived from the incident angle $\beta_{in}$, and a refractive index $n_a$ ($n_b$) of the layer 1a (layer 1b) according to the Snell's law. It should be noted that the incident angle $\beta_{in}$, and the refractive index $n_a$ ($n_b$) of the layer 1a (layer 1b) are known, and the refractive indices $n_a$ and $n_b$ are recorded in the single-layer-film characteristic recording unit 12a. Moreover, the thickness of the layer 1a is $d_a$.

$$\alpha_a (\cos \beta_t / 2d_a) \times \ln(I_{met-a}/I_{ref})$$

$$R_{sur-a} = I_{sur-a}/I_{ref} \qquad (1)$$

An absorption coefficient $\alpha_b$ of the terahertz wave and a surface reflectance $R_{sur-b}$ of the terahertz wave in the layer 1b recorded by the single-layer-film characteristic recording unit 12a are as follows. Moreover, the thickness of the layer 1b is $d_b$.

$$\alpha_b = -(\cos \beta_t / 2d_b) \times \ln(I_{met-b}/I_{ref})$$

$$R_{sur-b} = I_{sur-b}/I_{ref} \qquad (2)$$

The interface reflectance $R_{int}$ recorded by the single-layer-film characteristic recording unit 12a is a reflectance of the boundary surface between the layer 1a and the layer 1b when the layers 1a and 1b are overlapped, and is represented as follows. It is assumed that a complex refractive index $n_2 + jk_2$ of the layer 1a and a complex refractive index $n_3 + jk_3$ of the layer 1b are known. It should be noted that $n_2$ and $n_3$ are respectively the same as the refractive indices $n_a$ and $n_b$ of the layers 1a and 1b.

$$R_{int} = \{(n_2-n_3)^2 + (k_2-k_3)^2\}/\{(n_2+n_3)^2 + (k_2-k_3)^2\} \qquad (3)$$

The single-layer-film characteristic recording unit 12a records the absorption coefficients $\alpha_a$ and $\alpha_b$, the surface reflectance $R_{sur-a}$ and $R_{sur-b}$, and the interface reflectance $R_{int}$, for example.

Further, the single-layer-film characteristic recording unit 12a records a reflectance $R_{sub}$ (substrate reflectance) of a boundary surface between the layer 1b and the substrate 20, for example. The substrate reflectance $R_{sub}$ is represented as follows. It is assumed that a complex refractive index of the substrate $n_4+jk_4$ of the substrate 20 is known.

$$R_{sub} = \{(n_3-n_4)^2+(k_3-k_4)^2\}/\{(n_3+n_4)^2+(k_3+k_4)^2\} \quad (4)$$

It should be noted that variables relating to the layers 1a and 1b are defined in the following table.

|  | LAYER 1a | LAYER 1b |
|---|---|---|
| THICKNESS | $d_a$ | $d_b$ |
| ABSORPTION COEFFICIENT | $\alpha_a$ | $\alpha_b$ |
| SURFACE REFLECTANCE | $R_{sur-a}$ | $R_{sur-b}$ |
| REFRACTIVE INDEX | $n_a(=n_2)$ | $n_b(=n_3)$ |
| COMPLEX REFRACTIVE INDEX | $n_2 + jk_2$ | $n_3 + jk_3$ |

The measurement condition input unit 12b serves to input amplitudes $I_{ref-ab}$ of frequency components, and an incident angle $\beta_{in-ab}$ for the terahertz wave to be made incident to the object to be measured 1, an arrangement of the layers in the object to be measured 1 (the layer 1a is on the layer 1b), and a thickness d of the object to be measured 1 (a sum of the thicknesses $d_a$ and $d_b$ of the layers 1a and 1b) into the layer analysis device 10. This input is carried out by a user of the electromagnetic wave measurement device 100, for example.

The amplitude $I_{ref-ab}$ and the incident angle $\beta_{in-ab}$ of the frequency component of the terahertz wave to be made incident by the electromagnetic wave output device 2 to the object to be measured 1 can be the same values as the amplitude $I_{ref}$ and the incident angle $\beta_{in}$ of the frequency component of the terahertz wave used to generate the recorded content of the single-layer-film characteristic recording unit 12a. Hereinafter, it is assumed that the amplitude $I_{ref-ab}$ and the incident angle $\beta_{in-ab}$ are the same values as the amplitude $I_{ref}$ and the incident angle $\beta_{in}$, and are denoted by $I_{ref}$ and $\beta_{in}$.

The quantitative model deriving unit 12c derives a relationship (quantitative model) between a thickness indication quantity representing the thickness of at least any one of the layers (at least any one of the layers 1a and 1b) of the object to be measured 1, and the amplitude of the frequency component of the substrate-surface-reflected electromagnetic wave (refer to FIG. 2).

The quantitative model recording unit (thickness/amplitude characteristic recording unit) 12d records the relationship (quantitative model) derived by the quantitative model deriving unit 12c.

The thickness indication quantity is a value acquired by dividing the thickness of any one of the layers (such as the layer 1a) by the thickness of the object to be measured 1 (namely, the sum of the thicknesses of the layers 1a and 1b), for example. Moreover, the thickness indication quantity is a value acquired by dividing the thickness of any one of the layers (such as the layer 1a) by the thickness of the other layer (such as the layer 1b), for example.

A description will now be given of the embodiment of the present invention while it is assumed that a value (referred to as film thickness ratio) acquired by dividing the thickness $d_a$ of the layer 1a by the thickness d of the object to be measured 1 (namely, the sum of the thickness $d_a$ of the layer 1a and the thickness $d_b$ of the layer 1b) is used as the thickness indication quantity hereinafter.

Figure 6:
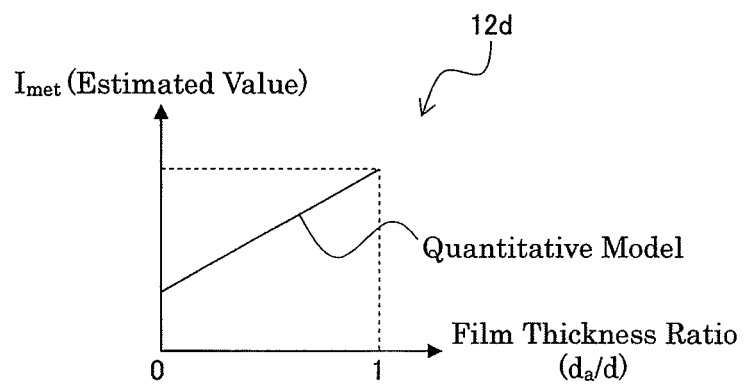
FIG. 6 is a diagram showing a recorded content of the quantitative model recording unit 12d for a certain frequency (such as $f_n$ [THz])

FIG. 6 is a diagram showing a recorded content of the quantitative model recording unit 12d for a certain frequency (such as $f_n$ [THz]). The quantitative model recording unit 12d records the correspondence between the film thickness ratio r ($=d_a/d$) and the amplitude $I_{met}$ of the frequency component of the substrate-surface-reflected electromagnetic wave for each frequency. The quantitative model estimates the amplitude $I_{met}$ of the frequency component of the substrate-surface-reflected electromagnetic wave by the recorded content of the single film characteristic recording unit 12a and the input by the measurement condition input unit 12b. It should be noted that the quantitative model is derived and recorded for each of frequencies (such as $f_n$=1.0, 1.1, and 1.2 [THz]). The quantitative model only needs to present the correspondence, and a chart, a table, and an equation are conceivable.

The amplitude $I_{met}$ of the frequency component of the substrate-surface-reflected electromagnetic wave is represented as follows. It should be noted that, referring to FIG. 2(a), the refraction angle $\beta_t$ is a refraction angle for the refraction by the layer 1a, and a refraction angle $\beta_{t1}$ is a refraction angle for the refraction by the layer 1b.

$$\begin{aligned} I_{met} &= I_{ref} \times (1-R_{sur-a})^2 \times (1-R_{int})^2 \times R_{sub} \times \exp(-2\alpha_a d_a/\cos\beta_t) \times \\ &\quad (-2\alpha_b d_b/\cos\beta_{t1}) \\ &= I_{ref} \times (1-R_{sur-a})^2 \times (1-R_{int})^2 \times R_{sub} \times \exp(-2\alpha_a dr/\cos\beta_t) \times \\ &\quad \exp(-2\alpha_b d(1-r)/\cos\beta_{t1}) \end{aligned} \quad (5)$$

The surface reflectance $R_{sur-a}$ means a degree of the reflection of the terahertz wave by the layer 1a, the interface reflectance $R_{int}$ means a degree of the reflection of the terahertz wave by the layer 1a and the layer 1b (interface between the layers 1a and 1b), and the substrate reflectance $R_{sub}$ means a degree of the reflection of the terahertz wave by the substrate 20.

The absorption coefficients $\alpha_a$ and $\alpha_b$ respectively mean degrees of the absorption of the terahertz wave by the layers 1a and 1b.

The quantitative models to be recorded in the quantitative model recording unit (thickness/amplitude characteristic recording unit) 12d are derived based on the reflection and the absorption of the terahertz wave (electromagnetic wave) in the respective layers in this way.

The quantitative model deriving unit 12c uses the surface reflectance $R_{sur-a}$ the interface reflectance $R_{int}$, the substrate reflectance $R_{sub}$, and the absorption coefficients $\alpha_a$ and $\alpha_b$ recorded in the single layer characteristic recording unit 12a out of the parameters required for estimating the amplitude $I_{met}$ of the frequency component of the substrate-surface-reflected electromagnetic wave. Moreover, the quantitative model deriving unit 12c uses the amplitude $I_{ref}$ and the thickness d of the object to be measured 1 input from the measurement condition input unit 12b. Further, the refraction angle $\beta_t$ and $\beta_{t1}$ are derived from the incident angle $\beta_{in}$ and the arrangement of the layers (the layer 1a is on the layer 1b) input by the measurement condition input unit 12b, and the refractive indices $n_a$ and $n_b$ of the layers 1a and 1b recorded in the single film characteristic recording unit 12a according to the Snell's law by the quantitative model deriving unit 12c.

The frequency component acquisition unit 12e acquires the amplitudes of the frequency components of the substrate-surface-reflected electromagnetic wave (refer to FIG. 2) acquired by the electromagnetic wave output device 2 making the terahertz wave incident to the object to be measured 1 (amplitude of each of the frequency components is $I_{ref}$), and the electromagnetic wave detector 4 detecting the terahertz wave. First, the frequency component acquisition unit 12e acquires the temporal waveform of the substrate-surface-reflected electromagnetic wave (detected as the voltage, for example) from the electromagnetic wave detector 4, and then applies the FFT (fast Fourier transform) to the temporal waveform, thereby acquiring the amplitudes $I_{met}$ of the frequency components. The amplitude of the frequency component is described as the description given of the $I_{ref}$. The frequency is omitted for the argument of the amplitude $I_{met}$ of the frequency component of the surface-reflected electromagnetic wave as the notation for the $I_{ref}$. The amplitude $I_{met}$ is an actually measured value.

The film thickness ratio deriving unit (thickness indication quantity deriving unit) 12f derives the thickness indication quantity (film thickness ratio r ($=d_a/d$)) based on the amplitude $I_{met}$ of the frequency component of the substrate-surface-reflected electromagnetic wave acquired by the frequency component acquisition unit 12e and the quantitative model (refer to FIG. 6), which is the recorded content of the quantitative model recording unit (thickness/amplitude characteristic recording unit) 12d.

Figure 7:
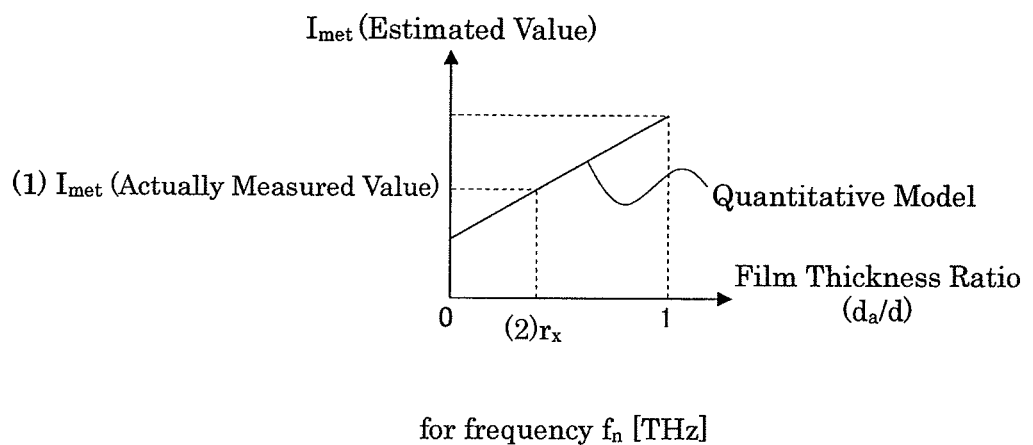
FIG. 7 is a chart for describing the derivation of the film thickness ratio r by the film thickness ration deriving unit (thickness indication amount deriving unit) 12f.

FIG. 7 is a chart for describing the derivation of the film thickness ratio r by the film thickness ration deriving unit (thickness indication amount deriving unit) 12f. It is assumed that the quantitative model is a chart in FIG. 7.

Referring to FIG. 7, a coordinate on a horizontal axis of a point having the amplitude $I_{met}$ (actually measured value) (refer to (1) in FIG. 7) of the frequency component of the substrate-surface-reflected electromagnetic wave acquired by the frequency component acquisition unit 12e as a coordinate on a vertical axis on the chart of the quantitative model is the thickness ratio $r_X$ (refer to (2) in FIG. 7).

The film thickness ratio $r_X$ is acquired for each of frequencies (such as $f_n$=1.0, 1.1, and 1.2 [THz]) from the quantitative model in this way.

For example, it is conceivable that an average of a film thickness ratio $r_X$ acquired from a quantitative model and an amplitude $I_{met}$ (actually measured value) for the frequency 1.0 THz, a film thickness ratio $r_X$ acquired from a quantitative model and an amplitude $I_{met}$ (actually measured value) for the frequency 1.1 THz, and a film thickness ratio $r_X$ acquired from a quantitative model and an amplitude $I_{met}$ (actually measured value) for the frequency 1.2 THz is output as the film thickness ratio $r_X$ of the object to be measured 1 from the film thickness ratio deriving unit 12f.

A description will now be given of an operation of the first embodiment.

(1) Derivation and Record of Quantitative Models

The electromagnetic wave measurement device 100 according to the first embodiment causes the quantitative model deriving unit 12c to derive the relationship (quantitative models) between the thickness indication quantity (film thickness ratio r ($=d_a/d$) and the amplitude $I_{met}$ of the frequency component of the substrate-surface-reflected electromagnetic wave (refer to FIG. 2) for each of the frequencies $f_n$ [THz] before the measurement of the object to be measured 1, and stores the relationships in the quantitative model recording unit 12d (refer to FIG. 6).

First, the electromagnetic wave measurement device 100 measures the incident terahertz wave (refer to FIG. 4), and derives the amplitudes $I_{ref}$. Then, the electromagnetic wave measurement device 100 measures the layers 1a and 1b (refer to FIG. 5), thereby deriving the amplitudes $I_{sur-a}$ ($I_{sur-b}$) of the frequency components of the surface-reflected component by the layers 1a and 1b, and derives amplitudes $I_{met-a}$ ($I_{met-b}$) of the frequency components of the substrate-surface-reflected component. The electromagnetic wave measurement device 100 derives the absorption coefficients $\alpha_a$ ($\alpha_b$) and the surface reflectances $R_{sur-a}$ ($R_{sur-b}$) in the layer 1a (layer 1b) based on the derived results (refer to Equations (1) and (2)), and records the absorption coefficients $\alpha_a$ ($\alpha_b$) and the surface reflectances $R_{sur-a}$ ($R_{sur-b}$) in the single-layer-film characteristic recording unit 12a. In addition, as described above (refer to Equations (3) and (4)), the interface reflectances $R_{int}$ and the substrate reflectances $R_{sub}$ are acquired and recorded.

Then, the measurement condition input unit 12b inputs the amplitudes $I_{ref}$ of the frequency components and the incident angle $\beta_{in}$ for the terahertz wave to be made incident to the object to be measured 1, the arrangement of the layers in the object to be measured 1 (the layer 1a is on the layer 1b), and the thickness d of the object to be measured 1 (the sum of the thicknesses $d_a$ and $d_b$ of the layers 1a and 1b).

The quantitative model deriving unit 12c derives the relationship between the thickness indication quantity (film thickness ration r ($=d_a/d$)) and the amplitude $I_{met}$ of the frequency component of the substrate-surface-reflected electromagnetic wave (refer to FIG. 2) for the each frequency $f_n$ [THz] based on the recorded content of the single-layer-film characteristic recording unit 12a and the input from the measurement condition input unit 12b as described above (refer to Equation (5)). The derived quantitative models are recorded in the quantitative model recording unit 12d (refer to FIG. 6).

(2) Measurement of Film Thickness Ratio r of the Object to be Measured 1

Then, the electromagnetic wave measurement device 100 according to the first embodiment measures the object to be measured 1, thereby deriving the film thickness ratio $r_X$ of the object to be measured 1 while referring to the quantitative models recorded in the quantitative model recording unit 12d.

First, referring to FIG. 2(a), the electromagnetic wave output device 2 outputs the terahertz wave toward the object to be measured 1. A part of the incident terahertz wave is reflected by the substrate 20, and passes through the object to be measured 1 (substrate-surface-reflected electromagnetic wave). The substrate-surface-reflected electromagnetic wave reaches the electromagnetic wave detector 4 later than the terahertz wave reflected by the surface of the layer 1a (surface-reflected electromagnetic wave) (refer to FIG. 2(b)). Therefore, the electromagnetic wave detector 4 distinguishes the substrate-surface-reflected electromagnetic wave and the surface-reflected electromagnetic wave from each other. Further, the electromagnetic wave detector 4 detects the substrate-surface-reflected electromagnetic wave as the voltage, and provides the frequency component acquisition unit 12e of the layer analysis device 10 with the correspondence with the time.

The frequency component acquisition unit 12e acquires the amplitudes $I_{met}$ (actually measured values) of the frequency components of the substrate-surface-reflected electromagnetic wave (refer to FIG. 2).

Referring to FIG. 7, the film thickness ratio deriving unit 12f receives the amplitude $I_{met}$ (actually measured value) from the frequency component acquisition unit 12e (refer to (1) in FIG. 7), reads an coordinate of the horizontal axis of the point in the chart of the quantitative model having the amplitude $I_{met}$ (actually measured value) as a coordinate of the vertical axis from the quantitative model recoding unit 12d, and sets the read coordinate as the film thickness ratio $r_X$ (refer to (2) in FIG. 7). The film thickness ratio $r_X$ is derived for each of the frequencies (such as $f_n$=1.0, 1.1, and 1.2 [THz]). Then, for example, the film thickness ratio $r_{XD}$ of the object to be measured 1 is derived by averaging the film thickness ratios $r_{XD}$ derived for the respective frequencies, for example.

According to the first embodiment, while the terahertz wave is irradiated on the object to be measured 1 having the layer structure (layers 1a and 1b), the film thickness ratio $r_{XD}$ of the object to be measured 1 can be measured by measuring the substrate-surface-reflected electromagnetic wave (refer to FIG. 2) without measuring the reflected wave by the boundary surface between the layers 1a and 1b. This is particularly useful for such a case that it is hard or impossible to measure the reflected wave by the boundary surface between the layers 1a and 1b.

The relationship (quantitative model) between the thickness indication quantity (film thickness ratio r ($=d_a/d$)) and the amplitude $I_{met}$ of the frequency component of the substrate-surface-reflected electromagnetic wave (refer to FIG. 2) is derived from the surface reflectances, the absorption coefficients, and the like according to the first embodiment. However, the derivation of the quantitative model recorded by the quantitative model recording unit (thickness/amplitude characteristic recording unit) 12d is not limited to this method, and may be derived by actually measuring the object to be measured 1 having a known film thickness ratio.

Figure 8:
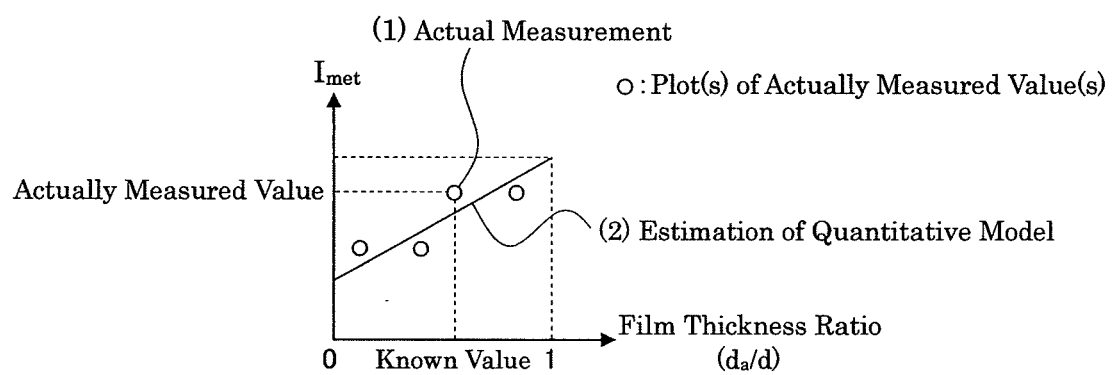
FIG. 8 is a diagram showing the derivation method for the quantitative model according to a variation of the first embodiment.

FIG. 8 is a diagram showing the derivation method for the quantitative model according to a variation of the first embodiment. First, (1) a object to be measured 1 having a known film thickness ratio is actually measured by the electromagnetic wave measurement device 100, thereby acquiring the amplitudes $I_{met}$ (actually measured values) of the frequency components of the substrate-surface-reflected electromagnetic wave from the frequency component acquisition unit 12e according to the variation of the first embodiment. Then, (2) a quantitative model is estimated from the amplitude $I_{met}$ (actually measured value) (acquired by (1)) of the frequency component of the substrate-surface-reflected electromagnetic wave associated with a known film thickness ratio for each of the frequencies (such as $f_n$=1.0, 1.1, and 1.2 [THz]). The estimation of the quantitative model can be acquired by, for example, assuming a chart representing the quantitative model as a straight line, and acquiring the line by means of the regression analysis (such as the least square method). Moreover, the principal component analysis may be applied to amplitudes $I_{met}$ (actually measured values) of the frequency components of the substrate-surface-reflected electromagnetic wave associated with known thickness ratios according to necessity.

It should be noted that the single-layer-film characteristic recording unit 12a, the measurement condition input unit 12b and the quantitative model deriving unit 12c are not used according to the variation of the first embodiment.

Second Embodiment

The electromagnetic wave measurement device 100 according to a second embodiment is different from the electromagnetic wave measurement device 100 according to the first embodiment in such a point that the layer analysis device 10 includes an error variation deriving unit 12g and a frequency range determination unit 12h, and a range of the frequency of the amplitudes $I_{met}$ of the frequency components acquired in the frequency component acquisition unit 12e is determined.

Such a point that the electromagnetic wave measurement device 100 includes the electromagnetic wave output device 2, the electromagnetic wave detector 4, and the layer analysis device 10, and measures the object to be measured 1 is the same as the first embodiment (refer to FIG. 1). Moreover, the configuration of the object to be measured 1 (refer to FIG. 2(a)) and such a point that the electromagnetic wave detector 4 detects the substrate-surface-reflected electromagnetic wave (refer to FIG. 2(b)) are the same as those of the first embodiment.

Figure 9:
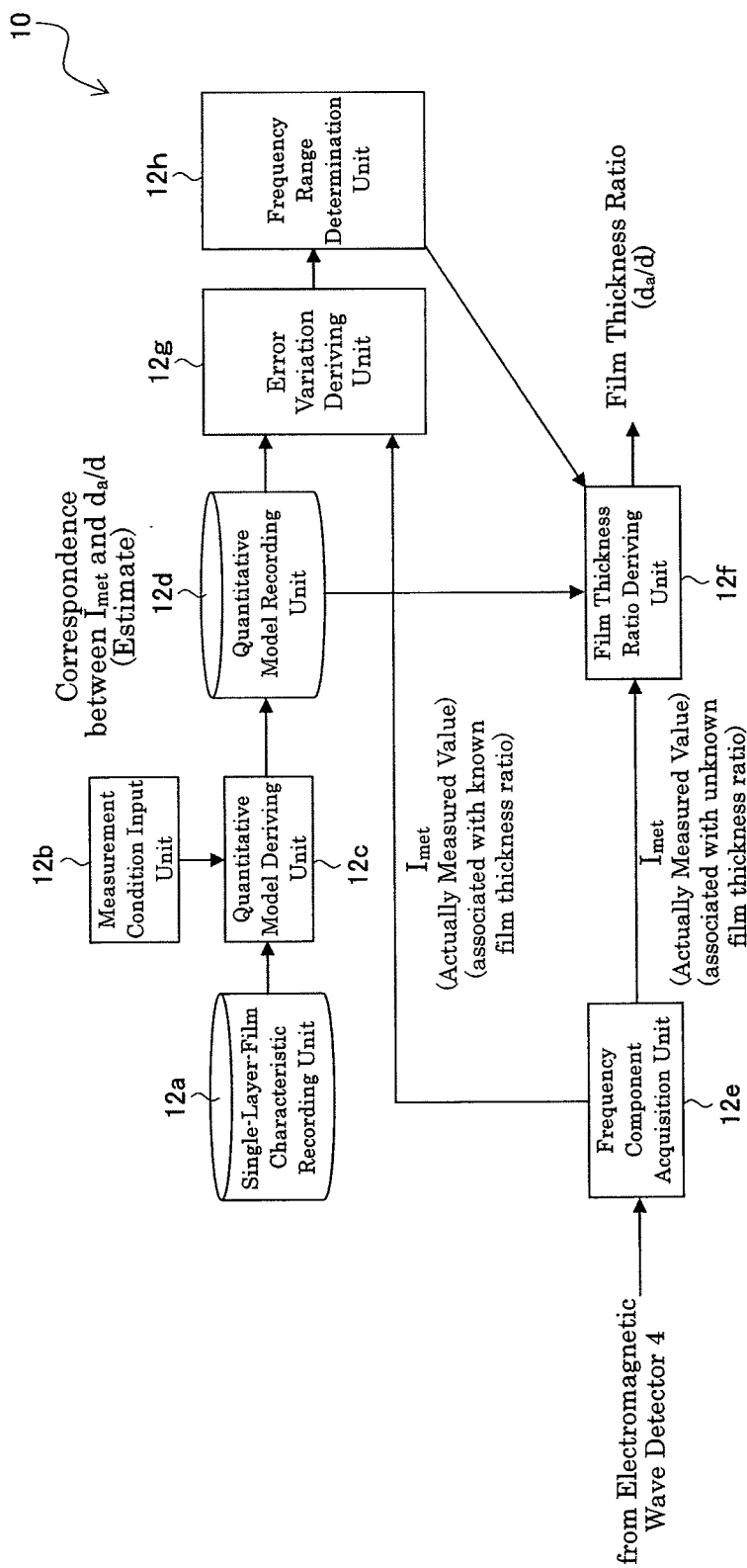
FIG. 9 is a functional block diagram showing a configuration of the layer analysis device 10 according the second embodiment.

FIG. 9 is a functional block diagram showing a configuration of the layer analysis device 10 according the second embodiment. The layer analysis device 10 includes the single-layer-film characteristic recording unit 12a, the measurement condition input unit 12b, the quantitative model deriving unit 12c, the quantitative model recording unit (thickness/amplitude characteristic recording unit) 12d, the frequency component acquisition unit 12e, the film thickness ratio deriving unit (thickness indication quantity deriving unit) 12f, the error variation deriving unit 12g, and the frequency range determination unit 12h. In the following section, like components are denoted by like numerals as of the first embodiment, and will be described in no more details.

The single-layer-film characteristic recording unit 12a, the measurement condition input unit 12b, the quantitative model deriving unit 12c, and the quantitative model recording unit (thickness/amplitude characteristic recording unit) 12d are the same as those of the first embodiment, and a description thereof is omitted.

The frequency component acquisition unit 12e acquires the amplitudes $I_{met}$ (actually measured values) of the frequency components of the substrate-surface-reflected electromagnetic wave from actually measured results of object to be measured 1 having known film thickness ratios before a measurement of a object to be measured 1 the film thickness ratio of which is unknown.

The error variation deriving unit 12g receives the measured values (actually measured values) of the amplitudes $I_{met}$ of the frequency components of the substrate-surface-reflected electromagnetic wave associated with the known film thickness ratios from the frequency component acquisition unit 12e. Further, the error variation deriving unit 12g derives a variation of errors between respective thickness ratios acquired based on the recorded content (quantitative model) of the quantitative model recording unit (thickness/amplitude characteristic recording unit) 12d and the respective known film thickness ratios for the respective frequencies $f_n$ [THz] from the measured values of the amplitudes $I_{met}$ received from the frequency component acquisition unit 12e.

Figure 10:
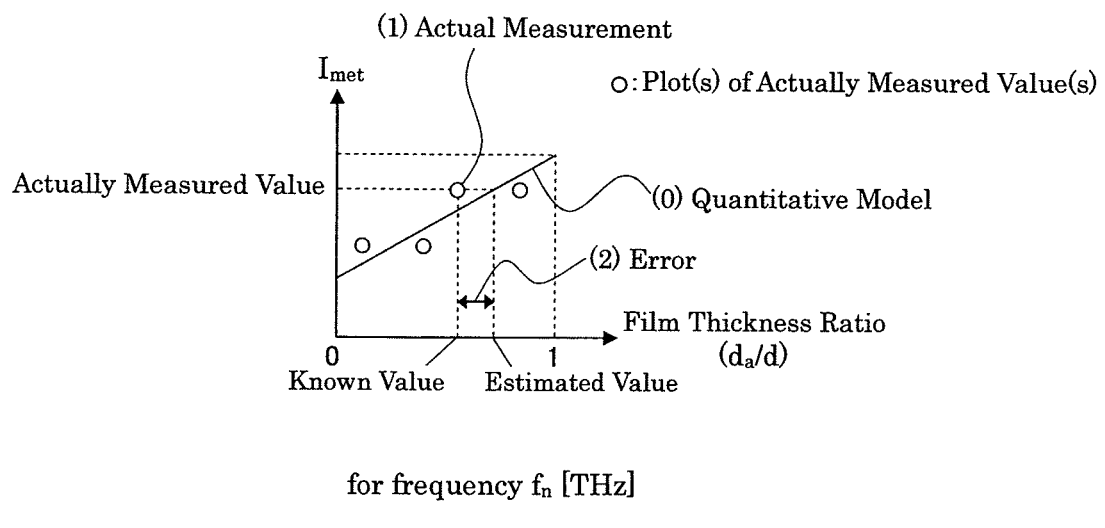
FIG. 10 describe a method of deriving the variation in error by the error variation deriving unit 12g for the component of the frequency $f_n$ [THz]

FIG. 10 describe a method of deriving the variation in error by the error variation deriving unit 12g for the component of the frequency $f_n$ [THz].

First, (0) quantitative models are stored in advance in the quantitative model recording unit (thickness/amplitude characteristic recording unit) 12d. On this occasion (1) the error variation deriving unit 12g acquires amplitudes $I_{met}$ (actually measured values) of the frequency components of the substrate-surface-reflected electromagnetic wave for known film thickness ratios from the frequency component acquisition unit 12e. Further, (2) the error variation deriving unit 12g acquires the film thickness ratio (estimated value) from the amplitude $I_{met}$ (actually measured value) based on the quantitative model (in which a coordinate on the horizontal axis of a point on a chart of the quantitative model having a coordinate on the vertical axis as the amplitude $I_{met}$ (actually measured value) is the film thickness ratio (estimated value)), and acquires (film thickness ratio (estimated value))-(known film thickness ratio (true value)) as the error.

The error variation deriving unit 12g acquires the errors of the respective amplitudes $I_{met}$ (actually measured values) acquired for the known film thickness ratios. The amplitudes $I_{met}$ (actually measured values) are acquired for plots for four points in the example in FIG. 10, and the errors are acquired for the four points. The error variation deriving unit 12g acquires a root mean square of the errors as a variation of the errors. In other words, the error variation deriving unit 12g acquires, as the variation of the errors, a square root of an average of the squared errors (a value acquired by dividing a sum of the squared errors of the four points by four in the example in FIG. 10).

The error variation deriving unit 12g derives the root mean square of the errors in this way for the respective components $f_n$ [THz] of the frequency. For example, the error variation deriving unit 12g acquires the root mean squares of the errors for $f_n$=0, 0.1, 0.2, . . . , 2.9, 3.9 [THz]. As the root mean square of errors decreases, the estimation of the film thickness ratio by the quantitative model becomes more accurate.

The frequency range determination unit 12h determines a range of the frequency $f_n$ [THz] of the amplitudes $I_{met}$ of the frequency components acquired by the frequency component acquisition unit 12e based on the derived result by the error variation deriving unit 12g.

The frequency range determination unit 12h averages the derived results by the error variation deriving unit 12g for a range (such as between 1.0 THz and 1.2 THz, $f_n$=1.0, 1.1, and 1.2 [THz]) of the frequency $f_n$ [THz]. For example, the frequency range determination unit 12h averages the error variation (root mean square) of the component at the frequency 1.0 [THz], the error variation (root mean square) of the component at the frequency 1.1 [THz], and the error variation (root mean square) of the component at the frequency 1.2 [THz].

In this way, the frequency range determination unit 12h averages the variations of the errors over the frequency range. Then, the frequency range determination unit 12h determines a range of the frequency $f_n$ so that the average of the error variations is minimized (or equal to or less than a predetermined value).

The range (such as between 1.0 THz and 1.6 THz, $f_n$=1.0, 1.1, 1.2, 1.3, 1.4, 1.5, and 1.6 [THz]) of the frequency $f_n$ determined in this way is fed to the frequency component acquisition unit 12e. Then, the frequency component acquisition unit 12e acquires amplitudes $I_{met}$ (actually measured values) of the frequency components of the substrate-surface-reflected electromagnetic wave in the determined range of the frequency $f_n$ from the actually measured result of the object to be measured 1 having an unknown film thickness ratio. A subsequent operation is the same as that of the first embodiment.

A description will now be given of an operation of the second embodiment.

First "(1) Derivation and record of quantitative model" is the same as that of the first embodiment, and a description thereof is therefore omitted.

Then, the frequency component acquisition unit 12e acquires the amplitudes $I_{met}$ (actually measured values) of the frequency components of the substrate-surface-reflected electromagnetic wave from the actually measured result of the object to be measured 1 having a known film thickness ratio. The amplitudes $I_{met}$ (actually measured values) are fed to the error variation deriving unit 12g. The error variation deriving unit 12g derives errors (refer to (2) of FIG. 10) in film thickness ratio from the quantitative models recorded in the quantitative model recording unit 12d and the amplitudes $I_{met}$ (actually measured values), and derives the variations (root mean squares) of the errors for the respective components of the frequency $f_n$ [THz].

The frequency range determination unit 12h averages the derived results by the error variation deriving unit 12g in a certain range of the frequency $f_n$ [THz] and determines a range of the frequency $f_n$ [THz] so that the average is minimum (or equal to or less than the predetermined value). The determined range (such as between 1.0 THz and 1.6 THz, $f_n$=1.0, 1.1, 1.2, 1.3, 1.4, 1.5, and 1.6 [THz]) of the frequency $f_n$ is fed to the frequency component acquisition unit 12e.

Then, "(2) Measurement of film thickness ratio r of the object to be measured 1" is approximately the same as that of the first embodiment. However, the frequency component acquisition unit 12e acquires the amplitudes $I_{met}$ of the frequency components in the range of the frequency $f_n$ [THz] determined by the frequency range determination unit 12h.

According to the second embodiment, the frequency component acquisition unit 12e acquires the amplitudes $I_{met}$ of the frequency components of the substrate-surface-reflected electromagnetic wave in the range of the frequency $f_n$ [THz] so that the variation in error of the estimation of the film thickness ratio by means of the quantitative models is minimum (or equal to or less than the predetermine value), the film thickness ratio deriving unit 12f derives the film thickness ratio of an object to be measured 1 having an unknown film thickness ratio, and the measurement error in film thickness ratio by the electromagnetic wave measurement device 100 can be minimum (or equal to or less than a predetermined value).

Third Embodiment

The electromagnetic wave measurement device 100 according to a third embodiment is different from the electromagnetic wave measurement device 100 according to the second embodiment in such a point that the thickness d (namely the sum of the thickness $d_a$ of the layer 1a and the thickness $d_b$ of the layer 1b) of the object to be measured 1 is measured.

Such a point that the electromagnetic wave measurement device 100 includes the electromagnetic wave output device 2, the electromagnetic wave detector 4, and the layer analysis device 10, and measures the object to be measured 1 is the same as that of the first embodiment (refer to FIG. 1). Moreover, the structure (refer to FIG. 2(a)) of the object to be measured 1 is the same as that of the first embodiment.

However, the third embodiment is different from the first embodiment in such a point that the electromagnetic wave detector 4 detects not only the substrate-surface-reflected electromagnetic wave (refer to FIG. 2(b) but also the surface-reflected electromagnetic wave. Namely, the electromagnetic wave detector 4 outputs not only the correspondence between the substrate-surface-reflected electromagnetic wave and the time (namely temporal waveform) as well as a correspondence between the surface-reflected electromagnetic wave and the time (namely temporal waveform). The correspondence between the substrate-surface-reflected electromagnetic wave and the time and the correspondence between the surface-reflected electromagnetic wave and the time are fed to a peak time point acquisition unit 12j.

It should be noted that the surface-reflected electromagnetic wave is the terahertz wave reflected by the surface of the layer 1a as described in the first embodiment. In other words, the surface-reflected electromagnetic wave is the electromagnetic wave (terahertz wave) made incident to the object to be measured 1, and is reflected by the surface of the object to be measured 1.

The electromagnetic wave detector 4 detects the surface-reflected electromagnetic wave as a voltage (or a power), for example. A description will be given while it is assumed that the electromagnetic wave detector 4 detects the surface-reflected electromagnetic wave (similarly to the substrate-surface-reflected electromagnetic wave) as a voltage (electric field) in this embodiment of the present invention.

Figure 11:
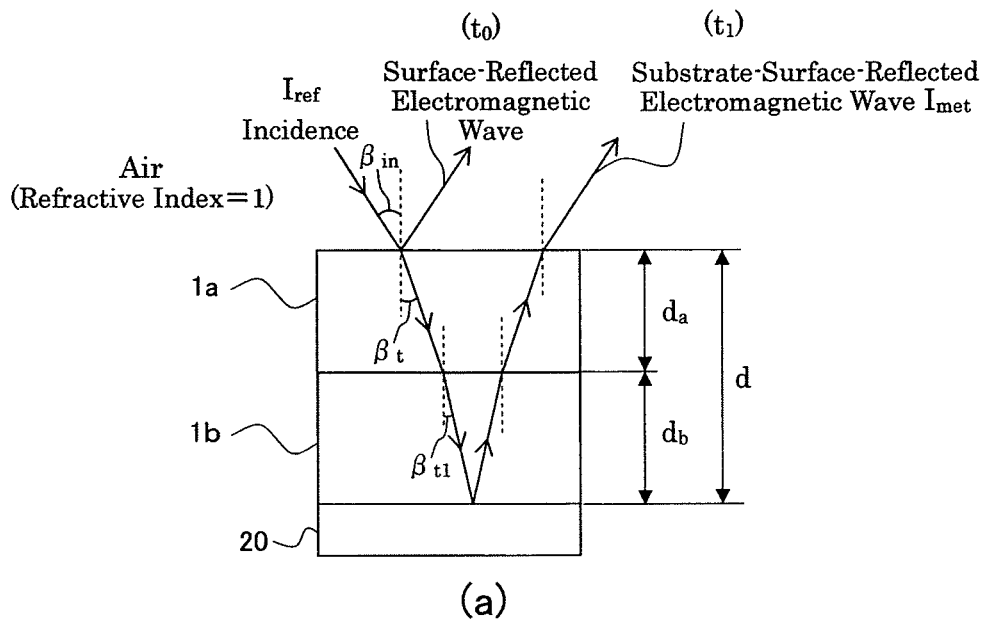
FIG. 11 includes a diagram (refer to FIG. 11(a)) showing the electromagnetic wave reflected by the object to be measured 1 having the two-layer structure according the third embodiment and the substrate 20, and a diagram (refer to FIG.
Figure 11:
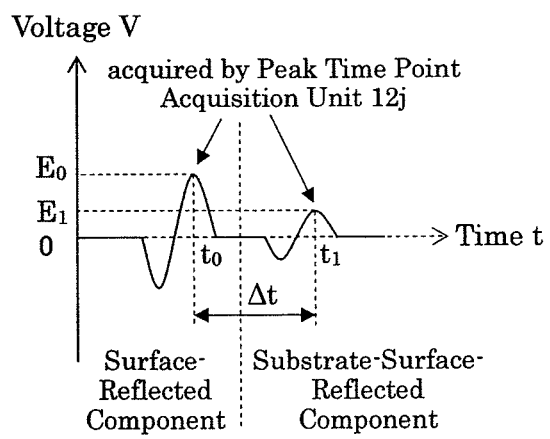

FIG. 11 includes a diagram (refer to FIG. 11(a)) showing the electromagnetic wave reflected by the object to be measured 1 having the two-layer structure according the third embodiment and the substrate 20, and a diagram (refer to FIG. 11(b)) showing timings when temporal waveforms of the reflected electromagnetic waves take extreme values.

Figure 12:
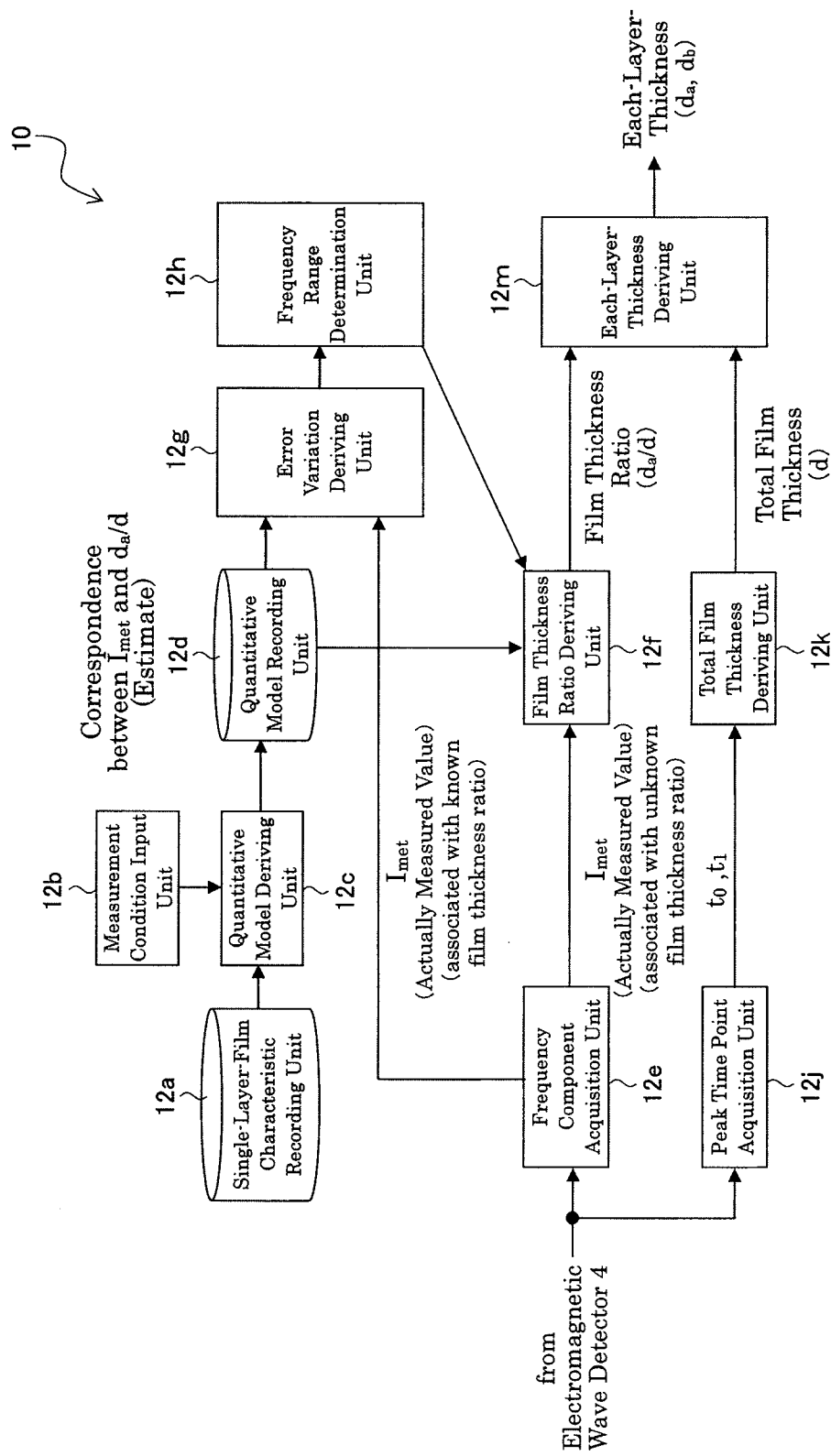
FIG. 12 is a functional block diagram showing a configuration of the layer analysis device 10 according the third embodiment.

FIG. 12 is a functional block diagram showing a configuration of the layer analysis device 10 according to the third embodiment. The layer analysis device 10 includes the single-layer-film characteristic recording unit 12a, the measurement condition input unit 12b, the quantitative model deriving unit 12c, the quantitative model recording unit (thickness/amplitude characteristic recording unit) 12d, the frequency component acquisition unit 12e, the film thickness ratio deriving unit (thickness indication quantity deriving unit) 12f, the error variation deriving unit 12g, the frequency range determination unit 12h, the peak time point acquisition unit (extreme timing acquisition unit) 12j, a total film thickness deriving unit (total thickness deriving unit) 12k, and an each-layer-thickness deriving unit (layer thickness deriving unit) 12m. In the following section, like components are denoted by like numerals as of the second embodiment, and will be explained in no more details.

The single-layer-film characteristic recording unit 12a, the measurement condition input unit 12b, the quantitative model deriving unit 12c, the quantitative model recording unit (thickness/amplitude characteristic recording unit) 12d, the frequency component acquisition unit 12e, and the film thickness ratio deriving unit (thickness indication quantity deriving unit) 12f are the same as those of the second embodiment, and a description thereof is therefore omitted.

The peak time point acquisition unit 12j receives the temporal waveforms (refer to FIG. 11(b)) of the surface-reflected electromagnetic wave and the substrate-surface-reflected electromagnetic wave detected by the electromagnetic wave detector 4.

The peak time point acquisition unit (extreme value timing acquisition unit) 12j further acquires the timings $t_0$ and $t_1$ at which the electric fields of the surface-reflected electromagnetic wave and the substrate-surface-reflected electromagnetic wave detected by the electromagnetic wave detector 4 take the extreme values.

On this occasion, referring to FIG. 11, the temporal waveform of the surface-reflected electromagnetic wave takes an extreme value $E_0$ at the timing (time) $t_0$. Moreover, the temporal waveform of the substrate-surface-reflected electromagnetic wave takes the extreme value $E_1$ at the timing (time) $t_1$. Then, the peak time point acquisition unit 12j outputs the timing to when the electric field of the surface-reflected electromagnetic wave takes the extreme value and the timing $t_1$ when the electric field of the substrate-surface-reflected electromagnetic wave takes the extreme value.

The total film thickness deriving unit (total thickness deriving unit) 12k derives the thickness d of the object to be measured 1 (total film thickness, namely the sum of the thickness $d_a$ of the layer 1a and the thickness $d_b$ of the layer 1b) from a time different $\Delta t$ between the timings to and $t_1$ acquired by the peak time point acquisition unit 12j.

It should be noted that the thickness d of the object to be measured 1 is represented as $d=c\Delta t/(2n_a)$ where c denotes the light speed if $n_a$ and $n_b$ are approximately equal to each other.

The each-layer-thickness deriving unit (layer thickness deriving unit) 12m derives the thickness of at least any one of the layers 1a and 1b of the object to be measured 1 based on the thickness indication quantity (film thickness ratio $r (=d_a/d)$) derived by the film thickness ratio deriving unit (thickness indication quantity deriving unit) 12f and the thickness d of the object to be measured 1 derived by the total film thickness deriving unit (total thickness deriving unit) 12k.

For example, the each-layer-thickness deriving unit 12m acquires the thickness $d_a$ of the layer 1a by multiplying the thickness d of the object to be measured 1 by the thickness ratio r. Moreover, the each-layer-thickness deriving unit 12m acquires the thickness $d_b$ of the layer 1b by subtracting the thickness $d_a$ of the layer 1a from the thickness d of the object to be measured 1.

It should be noted that the layer analysis device 10 according to the third embodiment can operate without including the error variation deriving unit 12g and the frequency range determination unit 12h.

A description will now be given of an operation of the third embodiment. It should be noted that a description is not given of the same operation as that of the second embodiment.

First, the peak time point acquisition unit 12j receives the temporal waveforms (refer to FIG. 11(b)) of the surface-reflected electromagnetic wave and the substrate-surface-reflected electromagnetic wave detected by the electromagnetic wave detector 4. It should be noted that a timing when the peak time point acquisition unit 12j receives the temporal waveforms may be before or after the frequency component acquisition unit 12e acquires the temporal waveform of the substrate-surface-reflected electromagnetic wave.

The timings $t_0$ and $t_1$ (refer to FIG. 11(b)) acquired by the peak time point acquisition unit 12j are fed to the total film thickness deriving unit 12k, and the total film thickness deriving unit 12k derives the thickness (total film thickness) d of the object to be measured 1. The thickness (total film thickness) d of the object to be measured 1 is fed to the each-layer-thickness deriving unit 12m.

An operation of the film thickness ratio deriving unit 12f for deriving the film thickness ratio is the same as the operation in the second embodiment, and a description thereof is therefore omitted.

The each-layer-thickness deriving unit 12m receives the film thickness ratio $r (=d_a/d)$ from the film thickness ration deriving unit 12f. The each-layer-thickness deriving unit 12m acquires the thickness $d_a$ of the layer 1a and the thickness $d_b$ of the layer 1b from the film thickness ratio $r (=d_a/d)$ and the thickness d of the object to be measured 1.

According to the third embodiment, even if the thickness d of the object to be measured 1 is not known, the thickness d of the object to be measured 1 is derived, and then, at least any one of the thickness $d_a$ of the layer 1a and the thickness $d_b$ of the layer 1b can be acquired.

Moreover, the above-described embodiment may be realized in the following manner. A computer may be provided with a CPU, a hard disk, and a media (such as a floppy disk (registered trade mark) and a CD-ROM) reader, and the media reader is caused to read a medium recording a program realizing the above-described respective components such as the layer analysis device 10, thereby installing the program on the hard disk. This method may also realize the above-described functions.

What is claimed is:

1. An electromagnetic wave measurement device comprising:
    an electromagnetic wave output device that outputs an electromagnetic wave having a frequency between 0.01 THz and 100 THz toward an object to be measured disposed on a substrate, the object to be measured including at least two layers;
    an electromagnetic wave detector that detects a substrate-surface-reflected electromagnetic wave, which has been made incident on the object to be measured, has been reflected by the substrate, and has passed through the object to be measured;

a frequency component acquirer that acquires an amplitude of a frequency component of the substrate-surface-reflected electromagnetic wave detected by the electromagnetic wave detector;

a thickness/amplitude characteristic recorder that records a relationship between a thickness indication quantity, representing a thickness of at least one of the layers of the object to be measured, and the amplitude of the frequency component of the substrate-surface-reflected electromagnetic wave; and a thickness indication quantity deriver that derives the thickness indication quantity, based on the amplitude of the frequency component of the substrate-surface-reflected electromagnetic wave acquired by the frequency component acquirer and the recorded content of the thickness/amplitude characteristic recorder, wherein the thickness indication quantity is a value acquired by dividing the thickness of one of the layers by a thickness of the object to be measured.

2. The electromagnetic wave measurement device according to claim 1, wherein the recorded content of the thickness/amplitude characteristic recorder is derived based on reflection and absorption of the electromagnetic wave in each of the layers.

3. The electromagnetic wave measurement device according to claim 1, wherein the recorded content of the thickness/amplitude characteristic recorder is estimated from a measured value of the amplitude of the frequency component of the substrate-surface-reflected electromagnetic wave associated with a known thickness indication quantity.

4. The electromagnetic wave measurement device according to claim 1, wherein the substrate is a metal plate.

5. The electromagnetic wave measurement device according to claim 1, comprising:

an error variation deriver that derives, from a measured value of the amplitude of the frequency component of the substrate-surface-reflected electromagnetic wave associated with a known thickness indication quantity, a variation of an error between a thickness indication quantity acquired based on the recorded content of the thickness/amplitude characteristic recorder and the known thickness indication quantity for each of frequency components; and a frequency range determiner that determines a range of the frequency of the amplitude of the frequency component acquired by the frequency component acquirer based on the derived result by the error variation deriver.

6. The electromagnetic wave measurement device according to claim 1, wherein the electromagnetic wave detector further detects a surface-reflected electromagnetic wave, which is an electromagnetic wave that has been made incident on the object to be measured and has been reflected by a surface of the object to be measured, the electromagnetic wave measurement device further comprising:

an extreme value timing acquirer that acquires timings when electric fields of the substrate-surface-reflected electromagnetic wave and the surface-reflected electromagnetic wave that have been detected by the electromagnetic wave detector take extreme values;

a total thickness deriver that derives a thickness of the object to be measured from a time difference between the timings acquired by the extreme value timing acquirer; and a layer thickness deriver that derives a thickness of at least one of the layers of the object to be measured based on the thickness indication quantity derived by the thickness indication quantity deriver and the thickness of the object to be measured derived by the total thickness deriver.

7. An electromagnetic wave measurement method comprising:

outputting an electromagnetic wave having a frequency between 0.01 THz and 100 THz toward an object to be measured disposed on a substrate, the object to be measured including at least two layers;

detecting a substrate-surface-reflected electromagnetic wave, which has been made incident on the object to be measured, has been reflected by the substrate, and has passed through the object to be measured;

acquiring an amplitude of a frequency component of the detected substrate-surface-reflected electromagnetic wave;

recording a relationship between a thickness indication quantity, representing a thickness of at least one of the layers of the object to be measured, and the amplitude of the frequency component of the substrate-surface-reflected electromagnetic wave; and deriving the thickness indication quantity based on the acquired amplitude of the frequency component of the substrate-surface-reflected electromagnetic wave and the recorded content in the recording, wherein the thickness indication quantity is a value acquired by dividing the thickness of one of the layers by a thickness of the object to be measured.

8. An electromagnetic wave measurement device comprising:

an electromagnetic wave output device that outputs an electromagnetic wave having a frequency between 0.01 THz and 100 THz toward an object to be measured disposed on a substrate, the object to be measured including at least two layers;

an electromagnetic wave detector that detects a substrate-surface-reflected electromagnetic wave, which has been made incident on the object to be measured, has been reflected by the substrate, and has passed through the object to be measured;

a frequency component acquirer that acquires an amplitude of a frequency component of the substrate-surface-reflected electromagnetic wave detected by the electromagnetic wave detector;

a thickness/amplitude characteristic recorder that records a relationship between a thickness indication quantity, representing a thickness of at least one of the layers of the object to be measured, and the amplitude of the frequency component of the substrate-surface-reflected electromagnetic wave; and a thickness indication quantity deriver that derives the thickness indication quantity, based on the amplitude of the frequency component of the substrate-surface-reflected electromagnetic wave acquired by the frequency component acquirer and the recorded content of the thickness/amplitude characteristic recorder, wherein the thickness indication quantity is a value acquired by dividing the thickness of one of the layers by the thickness of another layer of the layers.

9. An electromagnetic wave measurement method comprising:

outputting an electromagnetic wave having a frequency between 0.01 THz and 100 THz toward an object to be measured disposed on a substrate, the object to be measured including at least two layers;

detecting a substrate-surface-reflected electromagnetic wave, which has been made incident on the object to be measured, has been reflected by the substrate, and has passed through the object to be measured;

acquiring an amplitude of a frequency component of the detected substrate-surface-reflected electromagnetic wave;

recording a relationship between a thickness indication quantity, representing a thickness of at least one of the layers of the object to be measured, and the amplitude of the frequency component of the substrate-surface-reflected electromagnetic wave; and deriving the thickness indication quantity based on the acquired amplitude of the frequency component of the substrate-surface-reflected electromagnetic wave and the recorded content in the recording, wherein the thickness indication quantity is a value acquired by dividing the thickness of one of the layers by the thickness of another layer of the layers.

* * * * *